(12) United States Patent
Lane et al.

(10) Patent No.: US 7,372,367 B2
(45) Date of Patent: May 13, 2008

(54) SYSTEMS AND METHODS FOR MEASURING HAND HYGIENE COMPLIANCE

(75) Inventors: Stephen Lane, McLean, VA (US);
Kevin Strauss, McLean, VA (US);
Mary Coyne, McLean, VA (US)

(73) Assignee: AMRON Corporation, McLean, VA (US)

( * ) Notice: Subject to any disclaimer, the term of this patent is extended or adjusted under 35 U.S.C. 154(b) by 0 days.

(21) Appl. No.: 11/169,746

(22) Filed: Jun. 30, 2005

(65) Prior Publication Data

US 2005/0248461 A1 Nov. 10, 2005

Related U.S. Application Data

(63) Continuation of application No. 10/052,354, filed on Jan. 23, 2002, now Pat. No. 6,975,231.

(60) Provisional application No. 60/263,159, filed on Jan. 23, 2001.

(51) Int. Cl.
*G08B 23/00* (2006.01)

(52) U.S. Cl. .............................. 340/573.1; 340/545.3; 340/691.6

(58) Field of Classification Search ............ 340/573.1, 340/539.23, 545.3, 556, 567, 611, 614, 691.6; 4/300, 420
See application file for complete search history.

(56) References Cited

U.S. PATENT DOCUMENTS

| | | | |
|---|---|---|---|
| 4,896,144 A * | 1/1990 | Bogstad | .................. 340/691.6 |
| 4,986,144 A | 1/1991 | Kobayashi et al. | |
| 5,202,666 A | 4/1993 | Knippscheer | |
| 5,812,059 A | 9/1998 | Shaw et al. | |
| 5,857,228 A * | 1/1999 | Waltenberger et al. | ........ 4/662 |
| 5,870,015 A * | 2/1999 | Hinkel | .................... 340/573.1 |
| 5,945,910 A * | 8/1999 | Gorra | ...................... 340/573.1 |
| 6,028,520 A | 2/2000 | Maehre | |
| 6,038,331 A * | 3/2000 | Johnson | ..................... 382/100 |
| 6,577,240 B2 * | 6/2003 | Armstrong | ............... 340/573.1 |
| 6,727,818 B1 * | 4/2004 | Wildman et al. | ........ 340/573.1 |

OTHER PUBLICATIONS

Lane, Stephen S., "Nosocomial Infection Control Through Handwashing Prompts," Computer Retrieval of Information on Scientific Projects, Abstract Display, Aug. 2, 2004.

* cited by examiner

*Primary Examiner*—Benjamin C. Lee
*Assistant Examiner*—Daniel Previl
(74) *Attorney, Agent, or Firm*—Arent Fox LLP

(57) ABSTRACT

A method of measuring hand hygiene compliance includes the steps of maintaining a computer database, and determining whether any person entered a first area independent of whether the any person includes a sensor. The method also includes the steps of determining whether the any person left the first area and entered a second area, and determining whether the any person performed hand hygiene before leaving the first area. Moreover, the method includes the step of sending information associated with whether the any person performed hand hygiene before leaving the first area to the computer database.

10 Claims, 6 Drawing Sheets

SYSTEMS AND METHODS FOR MEASURING HAND HYGIENE COMPLIANCE

CROSS-REFERENCE TO RELATED APPLICATIONS

The present application claims priority from and is a continuation of U.S. patent application Ser. No. 10/052,354, which is entitled "Systems and Methods for Improving Hand Hygiene Compliance," and was filed on Jan. 23, 2002 now U.S. Pat. No. 6,975,231, which claims priority from U.S. Provisional Patent Application No. 60/263,159, which is entitled "Prompts for Handwashing," and was filed Jan. 23, 2001, the disclosures of which are incorporated herein by reference in their entirety.

FIELD OF THE INVENTION

The present invention relates generally to systems and methods for obtaining compliance data associated with hand hygiene, and in particular, to systems and methods for obtaining hand hygiene compliance data in a patient care environment, such as a hospital, a nursing home, or the like.

BACKGROUND OF THE INVENTION

Infections, including nosocomial infections, are prevalent in all patient care facilities including hospitals and nursing homes. These infections pose a significant health risk to hospitalized patients by delaying healing, extending the length of hospitalization and increasing the human and financial cost of care. A nosocomial infection has been defined as "a localized or systemic condition that 1) resulted from adverse reaction to the presence of an infections agent or its toxin and 2) was not present or incubating at the time of admission to the hospital." Research reveals that several types of microorganisms can be transferred by hand to live hosts, thereby producing nosocomial infections.

Nosocomial infections delay healing, extend the length of hospitalization and increase the cost of care. Each year, approximately 2.4 million Americans acquire a nosocomial infection and 100,000 persons die as a result of such infections.

Handwashing is the linchpin of infection control. Failure to conduct handwashing after toileting or prior to contact with a patient places patients and health care workers at great risk for the development of nosocomial infections. While health care workers play a powerful role in reducing nosocomial infections, they have also been implicated in contributing to their increase by failing to perform handwashing prior to contact with a patient and after handling contaminated materials. Although health care workers are required to participate in annual infection control in service inspections, there is a discrepancy between classroom knowledge and applied knowledge of infection control. This discrepancy suggests that innovative strategies in infection control must be created in order to reduce the rate of nosocomial infections.

U.S. Pat. No. 5,945,910 discloses a handwashing and monitoring system that uses a sensor that signals the dispensation of a cleaning agent from a dispenser. A dual mode monitoring and reporting module includes an input element, an output element, a processor and memory. The module accepts data identifying an employee, receives a signal indicating dispensation of the cleaning agent and stores compliance data records.

U.S. Pat. No. 5,870,015 discloses an apparatus in which toilet use is monitored and audible messages are produced that instruct users of the toilet regarding steps in toilet use and hygiene. The apparatus includes a housing that is removably attached to the toilet. A switch arm is coupled with the toilet handle and sends an activity signal indicative of the switch arm position to electronic circuitry that activates the audible messages.

U.S. Pat. No. 5,812,059 discloses a method and system for enhancing hygiene. An activating device is located outside a work area, a hand cleaning station is located near the work area, and a deactivating device is associated with the hand cleaning station. Upon leaving a food handling area, an indicator worn by a worker is activated when the worker is near the activating device. The indicator is deactivated only when it is determined that the worker has used the hand cleaning station.

U.S. Pat. No. 5,202,666 discloses an automated device used to remind employees to wash their hands after toileting. Sensors are worn on credit card sized badges and mounted in bathroom ceilings and attached to soap dispensers and sinks. When an employee enters the bathroom, the ceiling unit sensor activates a blinking light on the badge. The light is deactivated once the employee pumps the soap dispenser and stands in front of the sink for at least 15 seconds.

U.S. Pat. No. 4,986,144 discloses a hand washing alert warning system designed to warn someone to wash their hands. A door activate system is armed when the door to the wash facility is opened or a toilet is flushed and is deactivated when it is determined that the person has washed their hands.

However, these existing systems have several problems associated with them. For example, they are relatively complex, there is no way to effectively force employees to wear badges, the batteries in the badges have to be replaced frequently and there is no way to monitor what an employee does between the time they wash their hands and the time they return to their work area. Moreover, in certain environments, e.g., a patient care environment in which certain health care employees belong to a union, it may be desirable to collect general compliance data associated with a group of employees without singling out individual employees. Nevertheless, the known systems described above collect individual specific compliance data.

SUMMARY OF THE INVENTION

Therefore, a need had arisen for systems and methods for measuring hand hygiene compliance which overcome these and other shortcomings of the related art. A technical advantage of the present invention is that hand hygiene compliance data may obtained without the use of individually worn sensors and without singling out individual employees during the process of obtaining the hand hygiene compliance data.

According to an embodiment of the present invention, a method of measuring hand hygiene compliance comprises the steps of (a) maintaining a computer database, (b) determining whether any person entered a first area independent of whether the any person includes a sensor, and (c) determining whether the any person left the first area and entered a second area. The method also comprises the steps of (d) determining whether the any person performed hand hygiene before leaving the first area, and (e) sending information collected in step (d) to the computer database.

According to another embodiment of the present invention, a method of measuring hand hygiene compliance comprises the steps of (a) maintaining a computer database, (b) determining whether any person entered a first area independent of whether the any person includes a sensor, and (c) determining whether the any person left the first area and entered a second area. The method also comprises the steps of (d) determining whether the any person performed hand hygiene before leaving the first area, (e) if it is determined that the any person performed hand hygiene before leaving the first area, sending this information to the computer database, and (f) if it is determined that the any person did not perform hand hygiene before leaving the first area, determining whether the any person performed hand hygiene in the second area. Moreover, the method comprises the steps of (g) if it is determined that the any person performed hand hygiene in the second area, sending this information to the computer database, and (h) if it is determined that the any person did not perform hand hygiene after entering the second area, sending this information to the computer database.

According to yet another embodiment of the present invention, a method of measuring hand hygiene compliance comprises the steps of (a) maintaining a computer database, and (b) determining whether any person flushed a restroom toilet. The method also comprises the steps of (c) if the any person flushed the restroom toilet, determining whether the any person performed hand hygiene within a predetermined amount of time after flushing the restroom toilet, and (d) sending information collected in step (c) to the computer database.

According to still yet another embodiment of the present invention, an apparatus for measuring hand hygiene compliance comprises means for detecting each of whether any person entered a first area independent of whether the any person includes means for communicating with the means for detecting, and whether the any person left the first area and entered a second area independent of whether the any person includes means for communicating with the means for detecting. For example, the means for detecting may comprise an IR beam breaker switch, a passive infra red motion detector, an IR proximity detector, a pressure sensitive floor pad switch, or the like. The apparatus also comprises means for determining whether the any person performed hand hygiene before leaving the first area, and means for determining whether the any person performed hand hygiene in the second area after leaving the first area. Moreover, the apparatus comprises means for transmitting information associated with whether the any person performed hand hygiene before leaving the first area and whether the any person performed hand hygiene in the second area after leaving the first area to a computer database.

BRIEF DESCRIPTION OF THE DRAWINGS

This invention will be described in detail with reference to the accompanying drawings wherein.

DETAILED DESCRIPTION OF THE INVENTION

Figure 1:
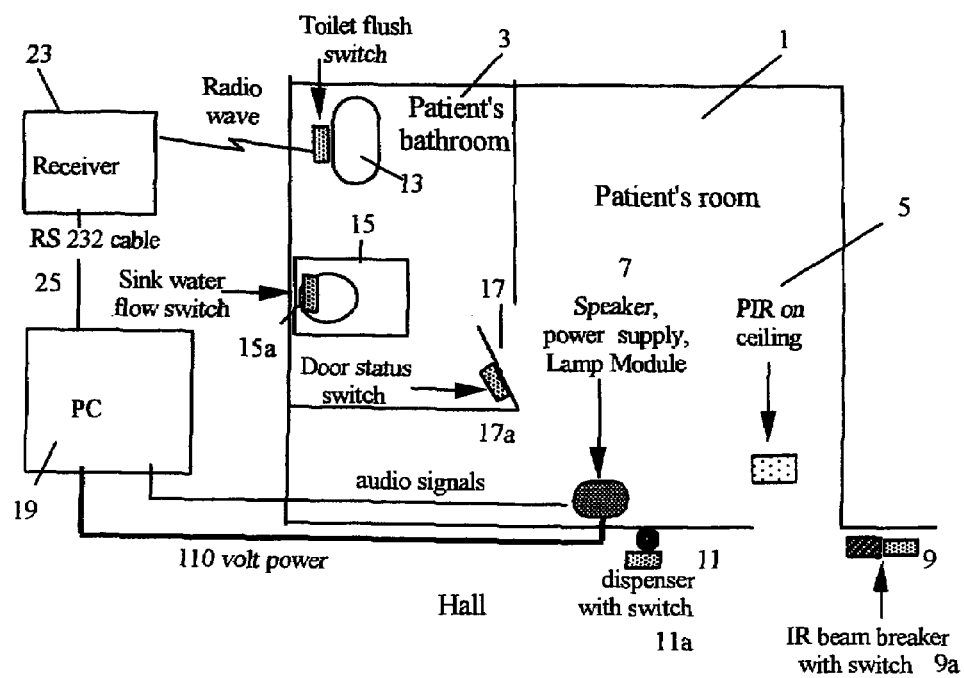
FIG. 1 is an illustration of the patient room with an adjoining bathroom according to a preferred embodiment of the present invention.

FIG. 1 illustrates a schematic view of a system according to a preferred embodiment of the present invention. The system includes patient room 1 and adjoining bathroom 3. As shown, located in patient room 1 is a thermal detector 5 and a speaker/appliance module assembly 7. Located proximate to patient room 1 is an IR (infrared) beam breaker 9/switch 9a and a dispenser 11/switch 11a. Located inside bathroom 3 is toilet 13/switch 13a, sink 15/water flow switch 15a and bathroom door 17/door status switch 17a. Computer 19 is connected via radio waves or radio frequency signals (RF) to switches 9a, 13a, 15a and 17a. Dispenser 11 is connected to computer 19 via standard AC power and receiver 23 is connected to computer 19 via a standard communications connection such as RS-232.

In a preferred embodiment, door status switch 17a transmits a signal to computer 19 indicating whether bathroom door 17 is open or closed, the toilet flush switch 13a transmits to computer 19 when the toilet handle has been depressed, and the sink water flow switch 15a transmits to computer 19 when water is flowing from the sink faucet.

IR beam breaker 9 comprises an infrared transmitter with a receiver and a reflector. The detector 5 detects motion inside patient room 1. An IR beam transmitted across the door, reflected at the other side, and detected at the transmitter indicated the presence of a person in the doorway to the room. Alternatively, pressure sensitive floor mats with electrical contacts or other appropriate sensing configuration may be used instead of IR beam breaker 9.

In a preferred embodiment, to detect toilet use, toilet flush switch 13a is attached to the toilet tank with a magnet on the handle for tank type toilets. The magnet and switch 13a are arranged so that flushing the toilet moves the magnet near the switch 13a triggering a signal to computer 19 that the toilet has been flushed. Alternatively, for toilets that flush by operation of a handle protruding from a pipe that can be moved in any direction to flush the toilet, a thin conductive sheet of metal may be wrapped around the toilet handle. The conductive sheet of metal is electrically insulated from the toilet handle. Wires from the insulated metal sheet and from the pipe into which the handle fits are connected to switch 13a. When the toilet 13 is flushed the conductive metal sheet touches the pipe, completing an electrical circuit. Switch 13a then sends a signal to computer 19 that the toilet 13 has been flushed.

In a preferred embodiment, sink water flow switch 15a is a non-conducting sleeve attached to the tap including electrodes placed inside. The electrodes are electrically isolated from the aerator body and are placed directly in the water stream when the water is flowing. Ordinary tap water is conductive because of dissolved electrolytes and therefore, water flowing over the electrodes conducts enough current between them to close the sink water flow switch 15a. Thus a signal from the switch 15a indicates water flowing in the sink indicating handwashing. In another embodiment, handwashing may be inferred from use of a liquid soap dispenser 11/switch 11a located near sink 15 that is used to directly sense the dispensation of soap and to provide the appropriate signal to computer 19.

The dispenser 11 consists of a tube containing liquid alcohol-based foam with a downward pointing spout on the bottom and may be mounted in a bracket on the wall just outside patient room 1. To detect foam dispensing, the dispenser's spout may be attached to a switch 11a or switch 11a may be placed on the wall behind the foam dispensing nozzle, in such a way that a person dispensing foam will press switch 11a. The foam dispenser may be mounted on a bracket on microswitches, which are mounted on the wall and connected in parallel to switch 11a. Alternately, a pressure actuated switch may be mounted on the wall in such a way that a person must press it to dispense foam. When a person presses the foam dispenser nozzle they will close one or more microswitches. The switches are connected to a status switch that transmits a signal indicating foam use to the computer. In yet another embodiment, a thermal detector may be mounted under the foam dispenser to note when a person places their hands on the spout to dispense foam.

At least one computer may be used to implement the present invention. A single computer, or perhaps more if required, will receive and process data from all sensors. Alternatively, additional computers may be used as required if the radio waves from the sensors are not strong enough to penetrate the walls between the computer and the most distant hospital rooms. In this case the additional computers are installed at separate locations from the first computer. Each computer can process data from those rooms nearest to it.

In a preferred embodiment the computer 19 communicates with sensors/switches via RF signals. However, it should be understood that radio waves may be replaced by higher frequency signals, optical signals, hard wires, or any well known communications system or method.

In a preferred embodiment, thermal detector 5 is an infrared motion detector that detects the time variations in differences in temperature in different directions in the detectors field of view. The devices observe the energy radiated by objects in their vicinity, but do not emit any radiation of their own, except for the RF signals transmitted to computer 19. When they detect motion they send an RF signal indicating their new state and a unique address. The switches/sensors contain a radio transmitter that transmits their unique address and a signal indicating an "on" status when their terminals are closed and a signal indicating an "off" status when those terminals are opened. Receiver 23 detects the signal and transmits it to computer 19 via RS-232 cable or any well know communication means. Computer 19 can then determine which switch changed state, and the new state as well.

In the preferred embodiment, data is collected and files are edited via a dedicated telephone line in communication with a central location. Computer 19 communicates with a computer at the central location so as to allow remote editing of files and remote data collection from computer 19 without physically being present at the patient facility. Alternatively, data may be collected and files edited on site.

Figure 2:
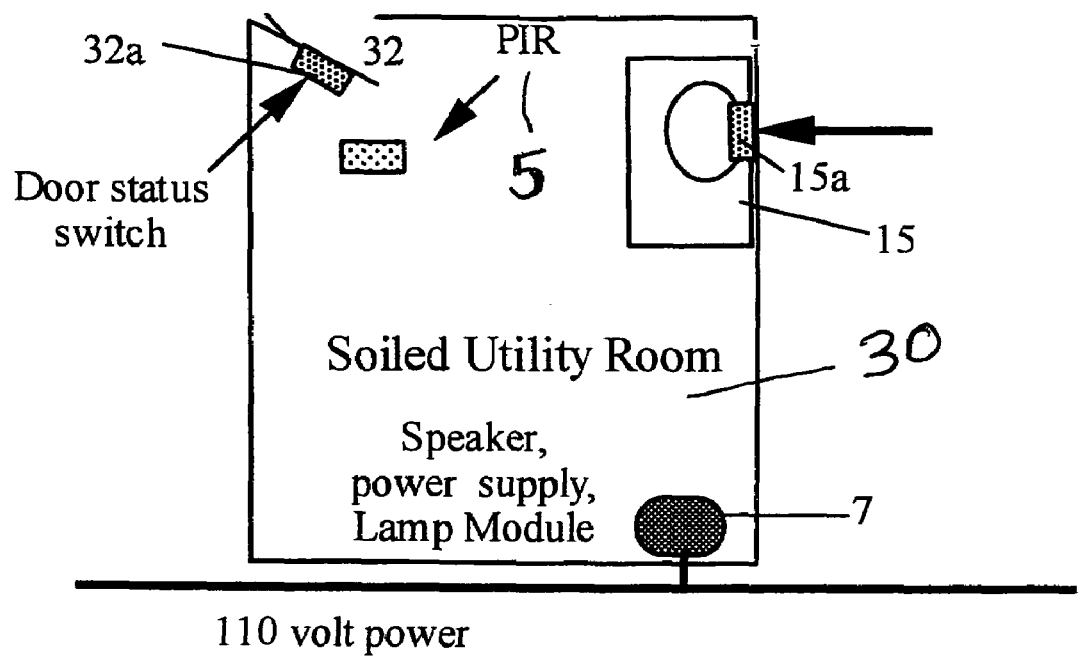
FIG. 2 is an illustration of a non-patient room according to a preferred embodiment of the present invention.

FIG. 2 is a schematic of a soiled utility room 30 illustrating a further usage of the present invention. As shown, located in the room is a detector 5, a sink 15/water flow switch 15a, and a speaker/power supply/appliance module 7. Attached to door 32 is door status switch 32a. A message is played in the soiled utility room 30 reminding those leaving the room to wash their hands if they open the door to leave without having washed their hands. If the door of the soiled utility room 30 is generally kept shut, door status switch 32a may be used without an IR beam or an outer floor mat. If the door is normally kept open, then IR beam breaker 9 may be used as in patient room 1.

Computer 19 is preferably equipped with a sound card to convert wav files in the computer memory, containing a digital representation of speech, into a voltage containing an analog representation of that speech. The audio signal is transmitted to speakers in hospital rooms and hallways via low voltage wires. Multiple speakers are controlled from a single computer, sending a message to one or more speaker at a time. In a preferred embodiment, messages are sent from the computer to the speakers via radio waves.

Figure 4A:
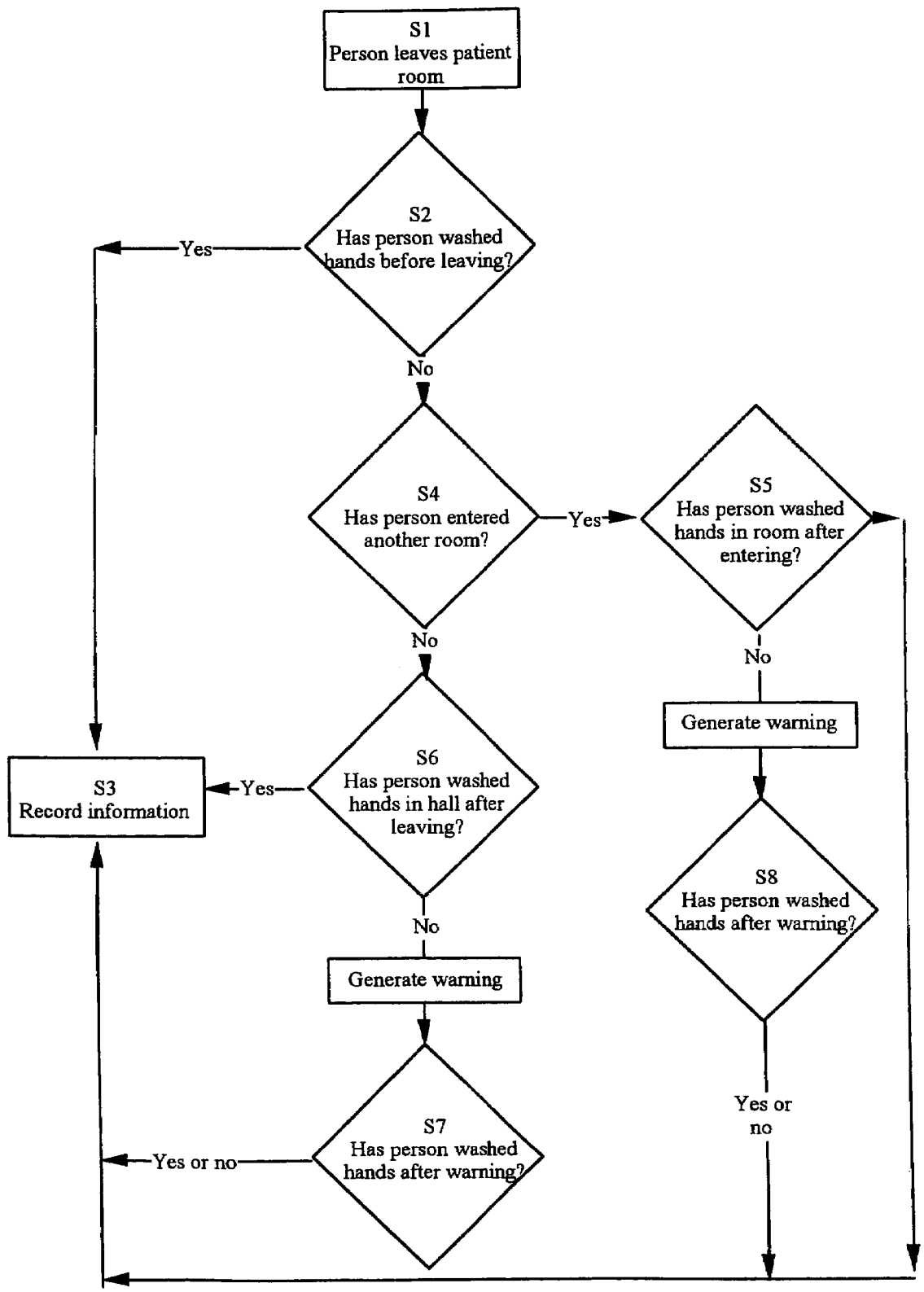
FIGS. 4a, 4b and 4c are flowcharts illustrating the process steps for FIGS. 1 and 2.
Figure 4B:
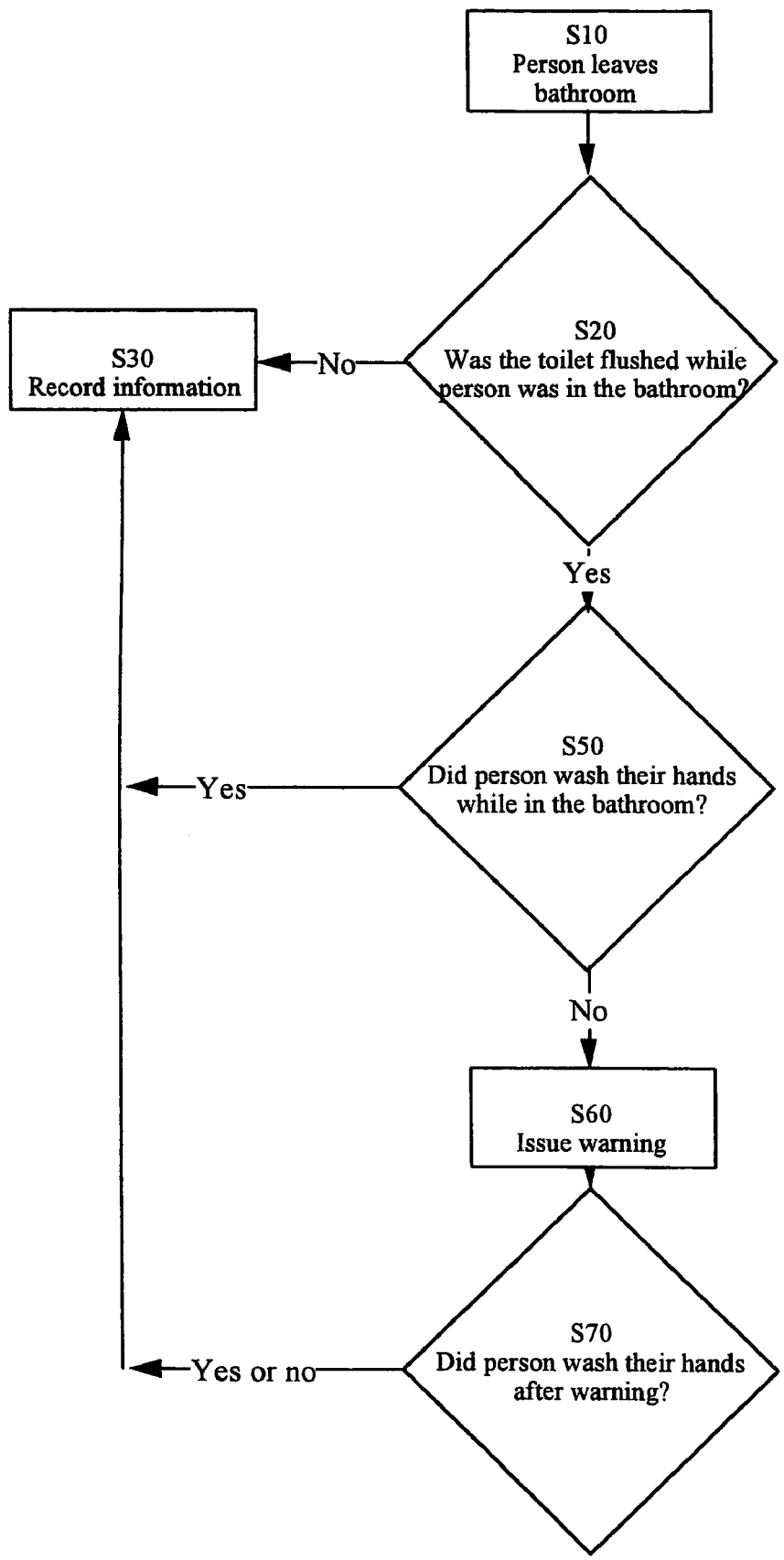
Figure 4C:
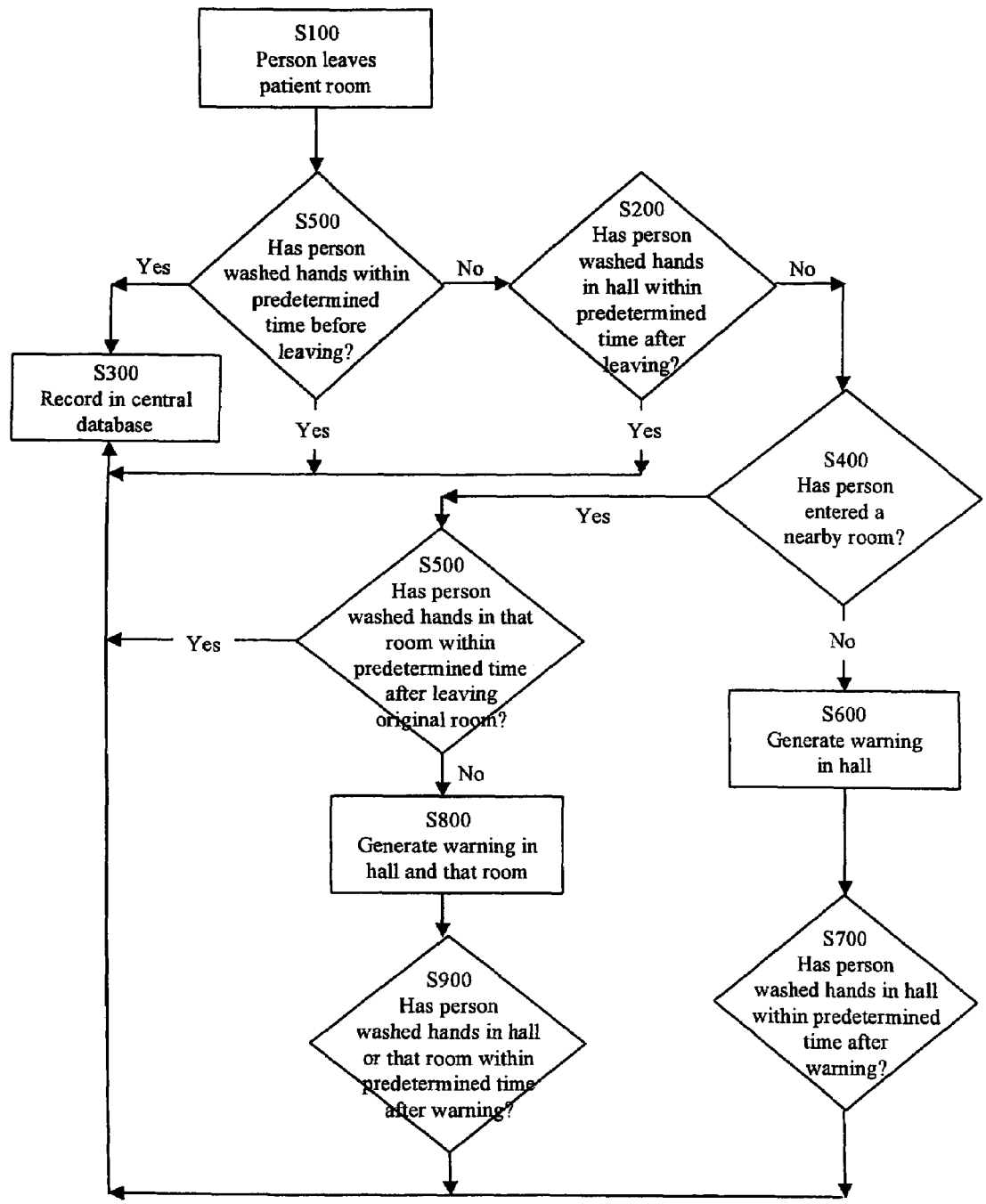

FIGS. 4a, 4b and 4c are flowcharts illustrating the systems of FIGS. 1 and 2. As shown in FIG. 4a, upon entering a patient's room at Step S1, if the person washed their hands within a set period of time, for example, approximately 10-20 seconds before entering the room at Step S2, or if the person washed their hands within a set period of time, for example, approximately 10-20 seconds after entering at Step S5, then just a record of the event is made at Step S3. In Step S6, if the person does not wash their hands within the set time period, they will hear a verbal prompt such as "wash your hands, please." In one embodiment, the present invention records the number of persons who a) enter the patient's room, b) require a prompt for handwashing, c) wash their hands when prompted to do so, and d) do not require a prompt for handwashing.

As shown in FIG. 4b, when a person leaves the patient bathroom at Step S10, it is determined that the person washed their hands in the bathroom at Step S20, then no prompt is issued and the information is recorded at Step S30. If it is determined that a person used the toilet, flushed it, and washed their hands and then flushed the toilet a second time at Step S40, if the person has not washed their hands at Step S50 an appropriate prompt, such as "wash your hands again, please" is issued at Step S60. If it is determined that a person used the toilet in Step S10 but that the person did not wash their hands before leaving the bathroom at Step S20, an appropriate prompt, such as "wash your hands please" is issued at Step S60. [Or, if the person simply flushes the toilet as they might after emptying a bedpan and they do not wash their hands, an appropriate prompt is issued at Step S60.] If it is determined at Step S80 that the person washed their hands after the warning prompt is issued, this information is sent to the central database in Step S30. If it is determined that the person washed their hands before leaving the bathroom as Step S20, then further checks for toilet flushes or handwashing are made at Steps S40 and S50. This process continues at Step S70 until the person leaves the bathroom. This information is sent to a computer database at Step S30.

As shown in FIG. 4c, when a person leaves the patient room at Step S100, and if it is determined at Step 500 that the person washed their hands before leaving the room, this information is recorded at Step S300 and no prompt is given. If the person does not wash before leaving and it is determined at Step S200 that the person washed their hands after leaving the room, then this information is recorded at Step S300 and no prompt is issued. If it is determined that the person did not wash their hands at Step S200 but entered a nearby room at Step S400, then at Step S500 it is determined if they washed their hands in that room. If is determined at Step S500 that the person washed their hands in the second room this information is sent to the central database at Step S300 and no prompt is issued. If it is determined that the person did not wash their hands at Step S500 a warning prompt is issued in the hall and in the room as Step S800. At Step S900 is determined if the person there after washed their hands and this information is sent the database as Step S300. If is determined at Step S400 that the person did not enter another room then a warning prompt is issued in the hall at Step S600. If is subsequently determined at Step S700 that the person thereafter washed their hands, this information is sent to the database at Step S300.

For example, when a person leaves the soiled utility room 30 illustrated in FIG. 2, if the person has already washed their hands, then only a record of the event is made. If the person has not washed their hands, when they leave they will hear a verbal prompt to such as "wash your hands, please."

In one embodiment, verbal prompts or audible prompts are used. However, although verbal prompts are effective, they may disturb patients. Verbal prompts can be used in areas such as the soiled utility room and staff bathroom and similar rooms without patients. Alternatively, visual prompts, such as flashing lights, may also be used. For example, a flashing light or flashing lighted sign may be used at all times and verbal prompts during daylight. Visual prompts may be used in rooms where voices are objectionable. Additionally, any combination of visual, audible, sensory, vibrating, or any other appropriate prompt is within the scope of the invention.

Figure 3:
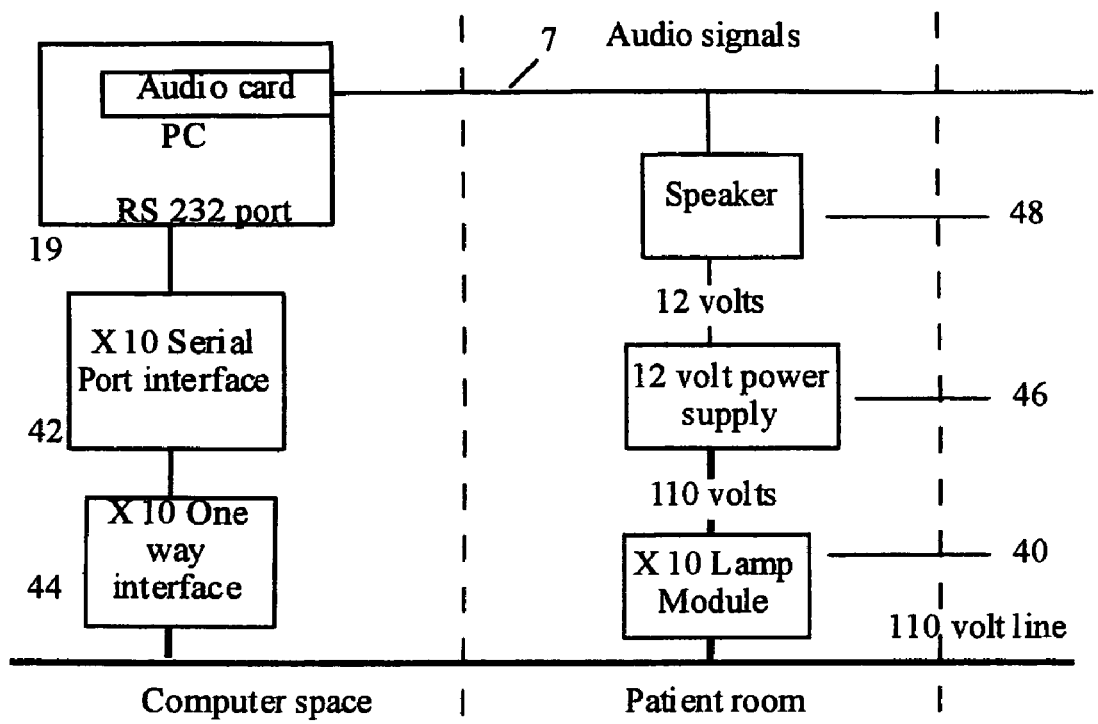
FIG. 3 is an illustration an audio message delivery system according to another embodiment of the present invention.

One embodiment of the speaker/power supply/appliance module 7 is illustrated in FIG. 3. A module 40 such as the X10 by Home Automation Systems™, Inc., is connected to an ordinary 110 volt wall socket. The signal is sent from computer 19 shown in FIG. 3 along the ordinary 110 volt power line, using the X10 Serial Port Interface 42 and the X10 Interface 44 shown in communication between computer 19 and the 110 volt line. Computer 19 may be connected to the same 110-volt lines as appliance module 40, but this is not required. A 12-volt DC power supply 46 is connected to module 40. The power supply output cable is connected to the power socket speaker 48. Alternatively, the flashing lighted sign may also be connected to module 40. In one example, the speaker audio jacks are connected in parallel to the audio/sound card in computer 19, as shown in FIG. 3. Alternatively, speaker 48 may plug directly into the X10 Appliance module and operate on 110-volt power.

The present invention determines when a person enters or leaves patient room 1 by comparing the sensor turn on times according to Table 1 and Table 2. Table 1 shows the sensor status when a person enters the room from the hall. "X" indicates time on the order of 5 seconds in the preferred embodiment, but is adjustable.

TABLE 1

Entry to room from hall

| Sensor\Status | On now? | On within the last X seconds? |
|---|---|---|
| IR Beam Breaker 9 | No | Yes |
| Detector 5 | Yes | Irrelevant |

In Table 1, the IR beam breaker 9 indicates that an object was in the door way within the last X seconds and detector 5 indicates that there is now something just inside the doorway.

TABLE 2

Exit from room to hall

| Sensor\Status | On now? | On within the last X seconds? |
|---|---|---|
| IR Beam Breaker 9 | Yes | Irrelevant |
| Detector 5 | No | Yes |

In Table 2, IR beam 9 is activated, indicating that a person is in the doorway. Detector 5 is shown as being activated within the last X seconds, indicating that a person has recently been just inside the patient's door.

Various embodiments of the invention have been disclosed herein. According to the present invention, a device senses a person entering into a room. A determination is made as to whether the person has cleansed their hands within a predetermined period of time. If it is determined that the person has cleansed their hands, the information is sent to a database. If it is determined that the person has not cleansed their hands, a warning signal is generated and as a result, the person is prompted to cleanse their hands.

Although various embodiments have been discussed, it is to be understood that while certain forms of the present invention, such as means for signaling, audio/visual warnings, have been illustrated, the invention is not to be limited to the specific forms or arrangements of parts described or shown. Although an inpatient environment has been described herein, the method and system is also applicable to other environments where hygiene is important such as food service or day care facilities. Given the above disclosure, many other features, modifications and improvements will become apparent to one skilled in the art.

What is claimed is:

1. A method of measuring hand hygiene compliance, comprising the steps of:
 (a) maintaining a computer database;
 (b) determining whether any person entered a first area independent of whether the any person includes a sensor;
 (c) determining whether the any person left the first area and entered a second area;
 (d) determining whether the any person performed hand hygiene before leaving the first area; and
 (e) sending information collected in step (d) to the computer database without reminding the any person to perform hand hygiene, if it is determined that the any person performed hand hygiene before leaving the first area, and upon reminding the any person to perform hand hygiene if it is determined that the any person did not perform hand hygiene before leaving the first area, wherein the step of determining whether the any person performed hand hygiene comprises pressing a pressure actuated switch to dispense foam, thereby closing at least one microswitch connected to a status switch that transmits a signal indicating foam use to the computer database.

2. A method of measuring hand hygiene compliance, comprising the steps of:
 (a) maintaining a computer database;
 (b) determining whether any person entered a first area independent of whether the any person includes a sensor;
 (c) determining whether the any person left the first area and entered a second area;
 (d) determining whether the any person performed hand hygiene before leaving the first area;
 (e) if it is determined that the any person performed hand hygiene before leaving the first area, sending this information to the computer database;
 (f) if it is determined that the any person did not perform hand hygiene before leaving the first area, determining whether the any person performed hand hygiene in the second area;
 (g) if it is determined that the any person performed hand hygiene in the second area, sending this information to the computer database;
 (h) if it is determined that the any person did not perform hand hygiene after entering the second area, sending this information to the computer database upon reminding the any person to perform hand hygiene, wherein the step of determining whether the any person performed hand hygiene comprises pressing a pressure actuated switch to dispense foam, thereby closing at least one microswitch connected to a status switch that transmits a signal indicating foam use to the computer database.

3. A method of measuring hand hygiene compliance, comprising the steps of:
   (a) maintaining a computer database;
   (b) determining whether any person flushed a restroom toilet included in a restroom;
   (c) if the any person flushed the restroom toilet, determining whether the any person performed hand hygiene before leaving the restroom; and
   (d) sending information collected in step (c) to the computer database,
   wherein the step of determining whether the any person performed hand hygiene comprises pressing a pressure actuated switch to dispense foam, thereby closing at least one microswitch connected to a status switch that transmits a signal indicating foam use to the computer database.

4. The method of claim 3, further comprising the step of determining whether the any person entered an area containing the restroom toilet.

5. A method of measuring hand hygiene compliance, comprising the steps of:
   (a) maintaining a computer database;
   (b) determining whether any person flushed a restroom toilet included in a restroom;
   (c) if the any person flushed the restroom toilet, determining whether the any person performed hand hygiene within a predetermined amount of time after flushing the restroom toilet; and
   (d) sending information collected in step (c) to the computer databases,
   wherein the step of determining whether the any person performed hand hygiene comprises pressing a pressure actuated switch to dispense foam, thereby closing at least one microswitch connected to a status switch that transmits a signal indicating foam use to the computer database.

6. An apparatus for measuring hand hygiene compliance, comprising:
   means for detecting, wherein the means for detecting is configured to detect each of:
   whether any person entered a first area independent of whether the any person includes means for communicating with the means for detecting; and
   whether the any person left the first area and entered a second area independent of whether the any person includes means for communicating with the means for detecting;
   means for determining whether the any person performed hand hygiene before leaving the first area;
   means for determining whether the any person performed hand hygiene in the second area after leaving the first area; and
   means for transmitting information associated with whether the any person performed hand hygiene before leaving the first area and whether the any person performed hand hygiene in the second area after leaving the first area to a computer database without reminding the any person to perform hand hygiene, if it is determined that the any person performed hand hygiene before leaving the first area, and upon reminding the any person to perform hand hygiene if it is determined that the any person did not perform hand hygiene before leaving the first areas;
   wherein the means for determining whether the any person performed hand hygiene before leaving the first area comprises a pressure actuated switch that dispenses foam, thereby closing at least one microswitch connected to a status switch that transmits a signal indicating foam use to the computer database.

7. The apparatus of claim 6, wherein the means for detecting comprises an IR beam breaker switch.

8. The apparatus of claim 6, wherein the means for detecting comprises a passive infra red motion detector.

9. The apparatus of claim 6, wherein the means for detecting comprises an IR proximity detector.

10. The apparatus of claim 6, wherein the means for detecting comprises a pressure sensitive floor pad switch.

* * * * *